United States Patent [19]
Eisenberg et al.

[11] Patent Number: 4,819,628
[45] Date of Patent: Apr. 11, 1989

[54] MOUTH-TO-MOUTH RESUSCITATOR DEVICE

[75] Inventors: Melvin I. Eisenberg; Mark Westfall, both of Skokie, Ill.

[73] Assignee: Plasco, Inc., Gurnee, Ill.

[21] Appl. No.: 76,949

[22] Filed: Jul. 23, 1987

[51] Int. Cl.$^4$ ............................................. A61M 16/00
[52] U.S. Cl. ............................ 128/203.11; 128/202.28
[58] Field of Search ...................... 128/202.28, 202.29, 128/203.11; 137/847

[56] References Cited

U.S. PATENT DOCUMENTS

| | | | |
|---|---|---|---|
| 3,387,624 | 6/1968 | Souey | 137/847 |
| 3,802,428 | 4/1974 | Sherman | 128/202.28 |
| 4,360,017 | 11/1982 | Barlett | 128/202.28 |
| 4,607,663 | 8/1986 | Raftis et al. | 137/847 X |
| 4,697,587 | 10/1987 | Marinkovitch | 128/203.11 |

FOREIGN PATENT DOCUMENTS 240878  9/1960  Australia .................. 128/202.28

Primary Examiner—A. Michael Chambers
Assistant Examiner—John C. Fox
Attorney, Agent, or Firm—Jerome Goldberg

[57] ABSTRACT

A resuscitator device for providing a physical shield between the rescuer and a victim requiring mouth-to-mouth resuscitation. The device comprises a flexible sheet having an opening centrally formed therein and a rigid tube secured to the sheet around the periphery of the opening for inserting into the mouth of the victim. A self closing one-way valve is contained in the tube and extends downward from the sheet opening and includes a flexible sleeve normally held closed at the outer end thereof by the action of a spring formed from a strip of rigid and flexible material secured to the outer end of the sleeve. The rescuer exhales a deep breath into the input of the valve via said opening in the sheet, to overcome the resilient force of the spring for discharging forced air into the mouth of the victim. After the rescuer has fully exhaled, the spring strip resiliently closes the valve to prevent any back flow of air, mist or liquid from the victim to the rescuer. Grooves are formed in the victim's side of the sheet to provide air pathways to the outside for air exhaled by the victim. A patch of an irregular non-smooth surface is also formed on the victim's side of the sheet to prevent the sheet from clinging to the nose, for allowing air flow out from the victim's nose.

24 Claims, 1 Drawing Sheet

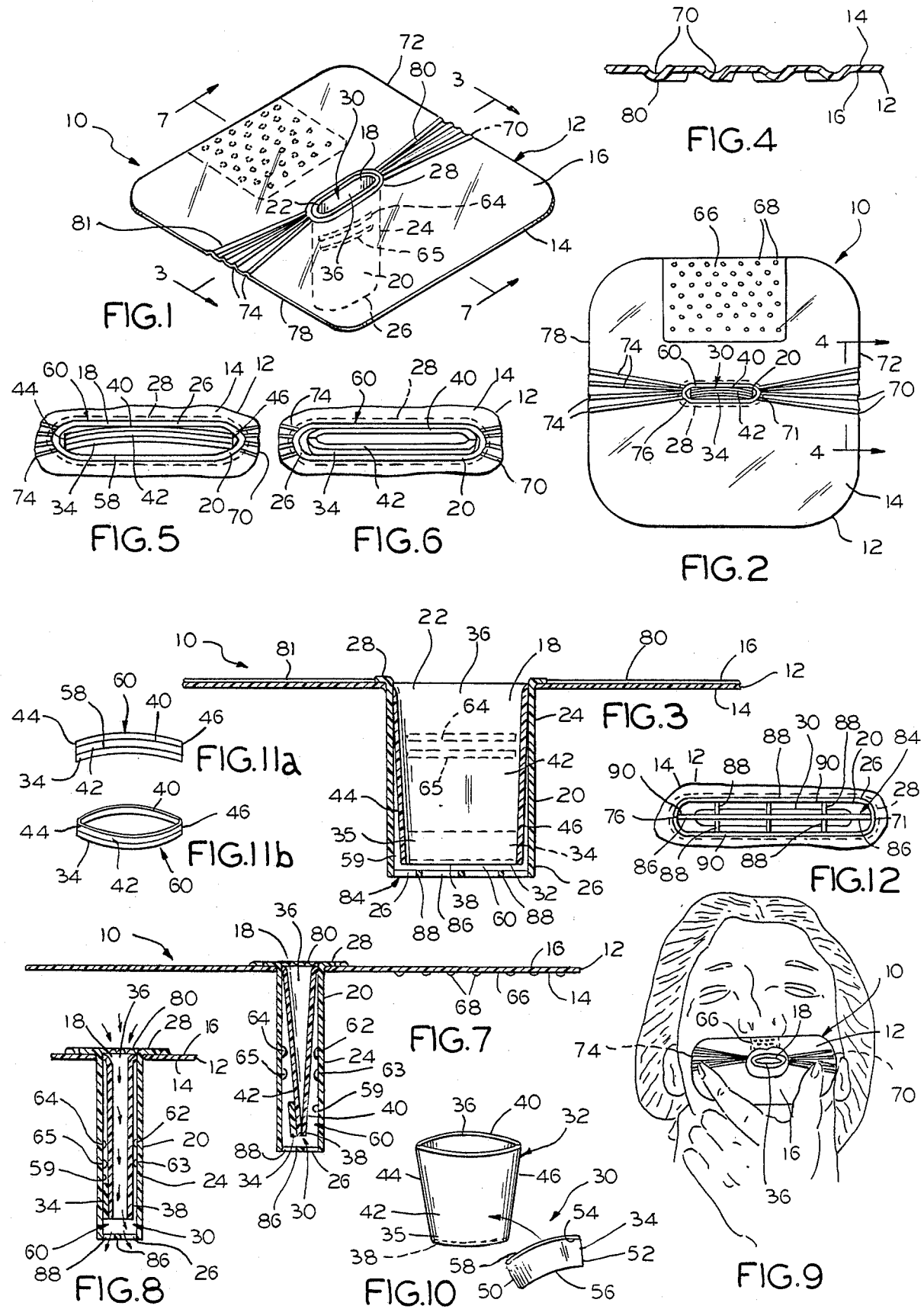

MOUTH-TO-MOUTH RESUSCITATOR DEVICE

BACKGROUND OF THE INVENTION

This invention relates generally to devices for providing mouth-to-mouth resuscitation or insufflation, and more specifically relates to devices having a physical barrier or shield between the mouth of the rescuer and the victim when providing mouth-to-mouth resuscitation to victims of suffocation, asphyxiation, cardiac arrest, drowning and the like.

Mouth-to-muth resuscitation is a first aid technique and a preferred method for reviving a non-breathing victim, when life or death may be determined from actions taken within seconds, by rapidly delivering large volumes of exhaled air under pressure to inflate the lungs and reactivate the normal breathing process. In this method, the victim is placed on his or her back, the mouth is opened to check and clear any airway obstruction and making sure the tongue is not lodged in the passageway to be used and is positioned in the lower cavity inside the mouth, the chin is pulled forward, the head is tilted backward, the nose or nostrils are pinched closed, then an air tight seal is made with the lips of the rescuer and the victim, and the rescuer commences to evenly exhale a deep breath under pressure into the victim's mouth; and then the lip seal is broken to enable another deep breath to be taken and the nose air pathways are opened in the event of any exhaling by the victim; and the process is repeated, until hopefully, the victim is able to exhale and to finally inhale unaided by the rescuer.

In the past, possible rescuers were reluctant to engage in mouth-to-mouth resuscitation for fear of contracting desease or illness from such contact with the victim. Generally, however, the person would assume the risk when there was no other alternative for saving the life of the victim. The individual attitude is considerably different today, for there is a mortal fear, which may or may not have any basis in fact, that any close or intimate cotnact could result in being stricken with the acquired immune deficiency syndrome ("AIDS") virus, particularly if the victim is suspected of being a drug user or a homosexual. Presently there is no known cure and only certain death after a person contracts the AIDS virus, and the number of reported AIDS cases are dramatically increasing throughout the world. In view of this, people will avoid or just refuse to give mouth-to-mouth resuscitation without any safeguard for shielding against direct and intimate contact. The subject invention provides such protection for the person giving mouth-to-mouth resuscitation or practicing this technique.

Various devices have been devised to shield the rescuer when applying mouth-to-mouth resuscitation. For example, U.S. Pat. No. 3,802,428 (1974), Sherman, discloses a mouth-to-mouth resuscitator comprising a flexible face mask having a central opening formed therein and extends over the mouth area of the person administering artificial respiration. A flexible tubular member is attached to the periphery of the central opening and depends therefrom for placement in the mouth of the victim. The tubular member acts as a one way valve and inflates when delivering air and collapses for preventing any air or fluid flow in the reverse direction.

In Sherman there is no immediate closure action of the air pathway through the valve, and moist air or fluids from the victim could flow or seep back to the rescuer. Moreover, the face mask of this device could sufficiently contact the mouth and nose to partially or fully prevent the victim from exhaling.

U.S. Pat. No. 4,050,457 (1977), Davidson, utilizes a face shield having a central mouth opening formed therein. The shield conforms to the contours of the face in the mouth and nose area, and particularly provides a covering over the patient's lips to permit mouth-to-mouth resuscitation without intimate contact. However, moist air and/or fluids from the victim could still be transferred to the rescuer.

None of the aforesaid Patents provide a resuscitator device having a one way valve which instantly closes after air is delivered to the victim, to prevent any back flow of air or liquid from the victim to the rescuer, and includes means for ensuring that the victim is not inhibited from exhaling.

SUMMARY OF THE INVENTION

The resuscitator device of this invention provides a physical shield between the rescuer and victim requiring mouth-to-mouth resuscitation. The device comprises a flexible sheet to conform to the contour of the face in the area of the mouth and nose. A mouth opening is formed centrally in the sheet. A rigid tube is bonded around the periphery of the mouth opening and depends downward therefrom to an output end. A self closing one way valve is positioned in the tube and includes a flexible sleeve having an open air inlet adjacent the mouth opening and an air outlet adjacent the output end of the tube. A spring strip is attached to the sleeve adjacent to the air outlet for tightly closing the air outlet.

The tube with the valve therein is inserted into the mouth of the victim and the sheet covers the mouth and nose area. The rescuer takes a deep breath and then makes a tight air seal around the mouth opening upon forcing his or her lips against the lips of the victim with the sheet sandwiched therebetween, and the deep breath is exhaled under pressure into the air valve via the mouth opening in the sheet. The forced air entering the valve spreads the sleeve walls apart and causes the spring strip to bow outwardly, for opening the valve and discharging the deep breath from the output end of the tube and into the mouth and lungs of the victim. The rigidity of the tube protects the valve and directs the forced air into the lungs.

After the exhaled deep breath has passed through the valve, the spring strip resiliently pulls the valve outlet closed, thereby instantly preventing any back flow of air, mist or liquid from the victim to the rescuer.

The resuscitator device herein is also suitable for use by the student or in a demonstration or practice with a manikin or another student for learning or practicing life saving techniques, particularly C.P.R. By each student having his or her own device a sanitary shield is thereby provided, which enables the same manikin to be continuously used without fear of contracting desease.

The plastic materials which are preferred for use in the construction of the subject resuscitator device may have a tendency to cling. In view of this, the device herein includes safeguards for overcoming any clinging problem which could effect its life saving operation. Therefore, ribs protrude inward from the inside surface of the tube to prevent the valve walls from clinging to the inside tube surface. Furthermore, a rough surfaced patch is constructed in the bottom or victim's side of the flexible sheet, which is operatively located adjacent the nose. The rough surface, which may comprise a plurality of spaced apart bumps, prevents the sheet barrier from sticking to the nose and blocking air flow out from the victim's nose.

Moreover, grooves are formed in the bottom or victim's side of the sheet and extend from adjacent the mouth opening to the outer edges of the sheet. Hence, if the sheet barrier tightly clings to the lips of the victim, even after the rescuer has removed the pressure he or she has been applying thereto when delivering forced air to the victim, any air exhaled from the victim's mouth could flow to the outside through these grooves.

BRIEF DESCRIPTION OF THE DRAWING

Referring to the drawing in which the same characters of references are employed to indicate corresponding similar parts throughout the several figures of the drawing.

FIG. 1 is a perspective top view of the resuscitator device, embodying the principals of the invention.

FIG. 2 is a bottom view of the resuscitator device without the safeguard arrangement.

FIG. 3 is a sectional view of the device, taken on the plane of the line 3—3 in FIG. 1, viewed in the direction indicated, and showing the air valve inside the tube.

FIG. 4 is a fragmentary sectional view, taken on the plane of the line 4—4 in FIG. 2, viewed in the direction indicated, to show the grooves for providing pathways for air exhaled from the mouth of the person being resuscitated.

FIG. 5 is a fragmentary enlarged bottom view of the device to illustrate the air valve outlet in a closed condition without the safeguard arrangement.

FIG. 6 is a view similar to FIG. 5, and showing the air valve outlet of the device in an open condition for forcing air into the person being resuscitated.

FIG. 7 is a view taken on the plane of the line 7—7 in FIG. 1, viewed in the direction indicated, and showing the air outlet of the air valve in a closed conditions.

FIG. 8 is a view similar to FIG. 7, but showing the air outlet of the air valve in an open condition.

FIG. 9 shows the resuscitator device positioned on the person being resuscitated.

FIG. 10 is a perspective view illustrating the flexible sleeve and the spring strip of the one way air valve spaced from the sleeve prior to being attached thereto.

FIG. 11a is a schematic bottom view of the valve outlet in a closed-condition.

FIG. 11b is a schematic bottom view of the valve outlet in an open condition.

FIG. 12 is a fragmentary view of the device to illustrate the safeguard arrangement secured to the output end of the tube.

DESCRIPTION OF THE PREFERRED EMBODIMENT

Referring now to the various Figures of the drawing, the reference numeral 10 indicates generally a resuscitator device for use as a physical barrier between a rescuer and a victim or patient when utilizing a procedure for resuscitating the patient, and is particularly suitable when engaging in Cardiac, Pulmonary Resusitation (C.P. R.), or in other situations when the victim is unable or has extreme difficulty breathing.

The resuscitator device 10 includes a flexible sheet 12 shown having a substantially square shape, although various other shapes and configurations, may be used, for positioning on the mouth or nose area of the face. The sheet 12 has a bottom side 14 (FIG. 2) and a top side 16 (FIG. 1). An oval mouth opening 18 is centrally formed in the sheet 12.

The sheet 12 is made from a transparent material impermeable by body fluids, moist air and microorganisms. An important characteristic of the material is its ability to conform to the contour of a victim's face. Preferably, the sheet 12 is made of a flexible plastic material such as a polyvinyl chloride (PVC) or similar material such as film-forming thermoplastics including nylon, polyethylene, polypropylene, polyvinyl acetate, soft cellulose acetate etc.

A hollow, oval, and rigid plastic tube 20 having a cross-sectional area just slightly less than the mouth opening 18 extends downward from the mouth opening 18, as viewed from FIG. 3. The tube 20 includes an input end 22, a body portion 24 and an output end 26. The input end 22 is positioned inside the mouth opening 18.

An oval flange 28 is integrally formed to and surrounds the input end 22 of the tube 20. The flange 28 rests on the top side 16 of the sheet 12 circumscribing the mouth opening 18, so that the tube 20 passes through the opening 12. The combined cross-sectional area of the flange 28 and the body portion 24 of the tube 20 exceeds the cross-sectional area of the hole 18. The flange 28 may be heat bonded or otherwise secured to the top side 16 of the sheet 12. The oval tube 20 and flange 28 are made from a semi-transparent rigid, elastomeric material.

A one way, self closing air valve indicated generally by the reference numeral 30 is positioned inside the tube 20. As may be seen from FIG. 10, the valve 30 includes a sleeve 32 and an arcuate spring strip 34 attached to the bottom portion 35 of the sleeve 32. Although the spring 34 is shown attached at the bottom, it may placed in a variety of positions closer to the air inlet end 36.

The sleeve 32 is open at the air inlet end 36 and also at the air outlet end 38, and is constructed from two substantially identical, confronting, thin, flexible walls 40,42 which are heat sealed along the opposite longitudinal marginal edges 44,46 thereof. The transverse or horizontal dimensions of the walls 40,42 progressively decrease and the marginal edges 44,46 taper inward from the air inlet end 36 to the air outlet end 38. Normally the portions of the confronting walls 40,42 at the outlet end 38 are flat and close together. The spring strip 34 resiliently forces the portions of the wall adjacent the air outlet end 38 into taut contact. The material for the walls 40,42 may be a suitable plastic such as a polyvinyle chloride sheet material.

The arcuate spring strip 34 is rigid and flexible, and may be constructed from a rigid polyvinyl chloride sheet or similar material. The spring strip 34 extends across the bottom portion 35 of the sleeve 32 adjacent the outlet end 38, and the side edges 50,52 of the spring strip 34 are heat sealed to the marginal edges 44,46 of the walls 40,42. Similar to the construction of the walls 40,42, the spring strip tapers inward from the top transverse edge 54 to the bottom transverse edge 56 (FIG. 10).

The arcuate spring strip 34 has a convex inner side 58 (FIGS. 5 and 11a). Normally the spring strip 34 resiliently forces the adjacent portions of the valve walls 40,42 into taut contact with the convex inner side 58, to thereby form an air seal between the walls 40,42 at the output end 38 of the sleeve 30.

The air inlet end 36 of the sleeve is opened and heat sealed to the oval inside surface of the tube 20 at the tube input end 22. Therefore, the walls 40,42 at the valve air inlet 36 are always spread apart. Also, the connection of the air inlet end 36 to the tube 20 seals the device 10 from any air or liquid flow from between the inside surface of the tube and the outside surfaces of the valve walls 40,42 to the top or rescuer's side 16 of the device 10.

The cooperation of the spring strip 34 with the walls 40,42 provides an air valve outlet 60. Initially, when no air is forced into the air valve inlet 36, the air valve outlet 60 is closed, since the arcuate spring strip 34 normally maintains the walls 40,42 in tight frictional contact with each other and wall 42 in taut contact with the convex side 58 of the spring strip 34.

As may be seen from FIG. 8, air forced into the valve inlet 36 causes the air valve outlet 60 to open as the walls 40,42 spread apart or bow outward from each other, to overcome the resilient closure force of the spring strip 34.

When air is no longer being forced into the valve inlet 36 the resilient force of the spring strip 34 pulls the adjacent portions of the walls 40,42 toward each other and into tight frictional contact, thereby returning the air valve outlet 60 to its closed position (FIGS. 7 and 11a).

A pair of ribs 62,63 are secured to and protrude inward from the inside surface 59 of the tube 20 adjacent to wall 40, and a pair of ribs 64,65 are secured to and protrude inward from the inside surface 59 adjacent to the wall 42. The ribs 62,63 prevent the wall 40 from fully contacting the inside surface of the tube 20 and possibly sticking thereto, the effect of which could prevent the air valve 30 from smoothly opening and closing. The ribs are shown extending horizontally as viewed in the drawing, but could extend vertically or in any other suitable manner.

A patch 66 having an irregular non-smooth surface caused by a plurality of small bumps 68. The patch 66 is positioned for contacting the nose or the area of the face adjacent thereto, to prevent any tight contact of the sheet 12 which could prevent the patient from exhaling from the nose upon being resuscitated.

A plurality of grooves or valleys 70 are formed in the bottom side 14 of the sheet 12 and radiate outward from adjacent the edge 71 of the flange 28 to the edge 72 of the sheet 12. Another plurality of grooves 74 are also formed in the bottom side 14 of the sheet 12 and radiate outward from the opposite edge 76 of the flange 28 to the opposite edge 78 of the sheet 12. The formation of the grooves 70,74 formed on the bottom side 14 of the sheet 12. cause respectfully peaks 80,81 to be formed on the top side 16. The grooves 70, and 72 provide air pathways to the outside from opposite ends the mouth of the patient, if the patient is trying to or is exhaling when the sheet 12 is in tight contact with the face. In operation, the grooves 70 would be on the left side of the patient's face, and the grooves 72 would be on the right side of the patient's face.

Turning now specifically to FIG. 12 of the drawing, it will be seen that a safeguard arrangement indicated generally by the reference numeral 82 is secured to the output end 26 of the tube 20. As shown, the safeguard arrangement 84 includes a longitudinal bar 86 (horizontal as viewed in FIG. 12) and three spaced apart transverse bars 88 (vertical as viewed in FIG. 12) attached to the longitudinal bar 86 and to opposite sides of the output end 26 of the tube 20. Notches 90 are formed inward from the outer end 26 of the tube 20 to receive the ends of the bars 86,88 and thereafter heat bonded or otherwise secured thereto. Similarly notches 92 are formed in the longitudinal bar 86 to support the bars 88, and thereafter the bars 88 are heat bonded or otherwise secured thereto.

The safeguard arrangement prevents the possibility of the tongue of the victim from inhibiting the operation of the valve 30 on the inside of the tube 20. Various configurations for the safeguard arrangement 84 are contemplated provided that it affords a screen or wall effect without preventing the desired air flow from the valve outlet 60 into the victim's mouth.

When resuscitating a victim with the device 10 or practicing the technique, the mouth of the victim is opened and the mouth is cleared of any obstruction; and the tongue is observed to be sure it is positioned in the lower part of the mouth. The tube 20 is inserted into the mouth of the victim, so that the bottom side 14 of the sheet 12 contacts the face of the victim and the top side 16 is opposed to the face of the rescuer. A deep breath is taken and the lips of the rescuer surrounds the mouth opening 18 and is pressed against the lips of the victim with the sheet 12 therebetween, thereby creating an air seal between the lips. The rescuer may brace the inner portions of the lips against the flange 28 to develope greater suction.

Then the deep breath is evenly exhaled under pressure into the valve inlet 36 via the mouth opening. The exhaled air causes the walls 40,42 to spread apart and has sufficient force to overcome the resilent closing force of the spring strip 34, thereby opening the air outlet valve 60 to discharge the exhaled air into the mouth of the victim via the tube output end 26. After the deep breath has been fully exhaled, the spring strip 34 closes the air outlet valve 60, and prevents and reverse flow of air and/or liquid from the victim to the rescuer. The rescuer takes another deep breath and repeats the resuscitation process, for delivering another large volume of air to the lungs of the victim. The shield afforded by the impermeable, flexible and contour forming sheet 12 and the instant acting self closing one way valve 30 provide a positive barrier separating the rescuer from the victim, which enables the rescuer to fully concentrate on the resusitation of the victim without concern that he or she may be contracting a deathly virus or disease.

Thus, after the device 10 is in place: tube 20 is inserted in victim's mouth and sheet 12 completely covers the victim's mouth and lips; the sheet 12 is flush against the victim's face; nostrils are pinched closed; and C.P.R. approved techniques may be used.

Various modifications of the invention of a mouth-to-mouth resuscitator device described herein, are within the spirit and scope of the invention, the scope of which is limited solely and defined by the appended claims.

We claim:

1. A mouth to mouth resuscitator device for use by a rescuer for resuscitating a victim, comprising:
    a sheet of flexible material having a top side and a bottom side, said sheet having a mouth opening formed therein at substantially the center thereof;
    a hollow rigid tube having an inner end and an outer end, said tube depending from the bottom side of said sheet from the inner end to the outer end, said inner end being in communication with said mouth opening;

a flexible sleeve positioned in said tube and having an air inlet end adjacent the tube inner end and an air outlet end adjacent the tube outer end; and a spring strip attached to said sleeve adjacent the air outlet end, said air inlet end being open and in communication with said mouth opening to permit air flow from the air inlet end to the air outlet end, said spring strip closing said sleeve at the air outlet end, air exhaled under pressure by the rescuer into said air inlet end causing said sleeve at the air outlet end to spread outward overcoming the resilient force of the spring strip and opening said air outlet end for discharging said air into the mouth of the victim, said spring strip resiliently closing said air outlet end after the rescuer has completed exhaling said air, and thereby preventing back flow of air and/or liquid from the victim to the rescuer.

2. The device of claim 1 includes:
a first rib protruding inward from the inside of said tube and positioned adjacent to one side of said sleeve; and
a second rib protruding inward from the inside of said tube and positioned adjacent to the other side of said sleeve, said ribs spacing said sleeve from the inside of said tube.

3. The device of claim 1, includes:
a rigid flange extending around said inner end of the tube and integrally formed thereto, said flange being secured to said sheet around the periphery of said mouth opening.

4. The device of claim 3, wherein said flange is dimensioned to provide a bracing surface for the inner portions of the upper and lower lips of the rescuer as the lips of the rescuer are pressed against the lips of the victim when said sheet is therebetween for providing an air seal between said lips.

5. The device of claim 3, wherein said flange is attached to the top side of the sheet and said tube passing through said mouth opening for extending downward from said bottom side of said sheet.

6. The device of claim 1, wherein said mouth opening is an oval shape and the inner end of the tube has an oval shape, said inner end of the tube forcing the lips of the victim slightly apart to enable the lips of the rescuer to easily make a tight air seal with the lips of the victim when said sheet is therebetween.

7. The device of claim includes:
air pathways formed in said sheet to permit exhaled air to flow from the victim to outside from said sheet.

8. The device of claim 7, wherein said air pathways include grooves formed in the bottom side of the sheet and extending from adjacent said mouth opening to an outer edge of the sheet.

9. The device of claim 7, wherein said air pathways include:
a first set of grooves formed in the bottom side of the sheet and radiating outward from adjacent one edge of the said mouth opening to one outer edge of the sheet; and
a second set of grooves formed in the bottom side of the sheet and radiating outward from adjacent an opposite edge of the mouth opening to an opposite outer edge of the sheet, said one and opposite outer edges of the sheet being juxtaposed respectively with the cheeks of the victim when the device is in the operative position.

10. The device of claim 1 includes:

a patch of an irregular surface formed in the bottom side of said sheet for positioning adjacent the nose area of the victim, to prevent blockage of air flow from the nose.

11. The device of claim 10, wherein said irregular surface includes a plurality of of bumps formed in said patch.

12. The device of claim 1, wherein said sleeve tapers inward from the air inlet to the air outlet, so that the smallest cross sectional area is adjacent the air outlet.

13. The device of claim 1, wherein said spring strip has an arcuate shape and the inner surface thereof is convex and resiliently pulls said sleeve at the outlet end into tight contact.

14. The device of claim 1 includes a safeguard device attached to the outer end of said tube to provide a blocking surface without effecting the desired air discharge into the mouth of the victim.

15. The device of claim 14 wherein said safeguard arrangement comprises:
a plurality of bars extending across the outer end of said tube.

16. The device of claim 15 includes a longitudinal bar extending across the outer end of the tube and attached thereto; and
a plurality of spaced apart transverse bars attached to said longitudinal bar and to opposite sides of said outer end of the tube.

17. The device of claim 15, wherein notches are formed at said outer end to receive opposite ends of said longitudinal and transverse bars.

18. A mouth to mouth resuscitator device for use by a rescuer for resuscitating a victim, comprising:
a sheet of flexible material having a top side for contacting the rescuer and a bottom side for contacting the victim, said sheet having a mouth opening formed therein at substantially the center thereof;
a hollow rigid tube insertible in the victim's mouth and having an inner end and an outer end, the inner end of said tube being secured to the periphery of said mouth opening and said tube extending outward therefrom to said outer end;
a self closing one-way valve is positioned inside said tube, said valve normally having a closed condition for preventing back flow of air and/or liquid flowing from the victim to the rescuer, said valve having an open condition when the rescuer exhales air under pressure into said valve via said mouth opening for discharging air into the mouth of the victim; and
a patch of an irregular surface formed on said bottom side of said sheet for positioning adjacent the nose of the victim when the device is in an operative position, for permitting air flow from said nose.

19. The device of claim 18, wherein said irregular surface includes a plurality of spaced apart bumps.

20. A mouth to mouth resuscitator device for use by a rescuer for resuscitating a victim, comprising:
a sheet of flexible material having a top side for contacting the rescuer and a bottom side for contacting the victim, said sheet having a mouth opening formed therein at substantially the center thereof;
a hollow rigid tube insertible in the victim's mouth and having an input end and an output end, the input end of said tube being secured to the periphery of said mouth opening and said tube extending outward therefrom to said output end;

a self closing one-way valve is positioned inside said tube, said valve normally having a closed condition for preventing back flow of air and/or liquid flowing form the victim to the rescuer, said valve having an open condition when the rescuer exhales air under pressure into said valve via said mouth opening and said input of the tube, for discharging air into the mouth of the victim; and air pathway means extending from adjacent said mouth opening at least one air pathway on the bottom side of the sheet extending from adjacent said mouth opening to an outer edge of the sheet.

21. The device of claim 20, wherein said air pathways include a plurality of grooves formed in the bottom side of the sheet.

22. The device of claim 20, wherein said air pathways include:

a first plurality of grooves formed in said bottom side of said sheet and extending outward from adjacent said mouth opening to an outer edge of the sheet operatively positioned adjacent the right cheek of the victim; and a second plurality of grooves formed in said bottom side of said sheet and extending outward from adjacent said mouth opening to the opposite outer edge of the sheet operatively positioned adjacent the left cheek of the victim.

23. A mouth to mouth resusitator device for use by a rescuer for resuscitating a victim, comprising:

a sheet of flexible material having a top side and a bottom side, said sheet having a mouth opening formed therein at substantially the center thereof;

a hollow rigid tube for inserting into the victim's mouth and having an inner end and an outer end, said inner end of the tube being secured to the periphery of said mouth opening and said tube extending outward therefrom to said outer end;

a self closing one-way valve is positioned inside said tube, said valve normally having a closed condition for preventing back flow of air and/or liquid flowing from the victim to the rescuer, said valve having an open condition when the rescuer exhales air under pressure into said valve via said mouth opening for discharging air into the mouth of the victim; and said valve including a thin, flexible, open ended sleeve and a spring strip, said sleeve being formed from two opposed confronting walls attached together at their marginal edges thereof, one end of the said sleeve being an air inlet and the opposite end of the sleeve being an air outlet, said spring strip being resiliently attached to the sleeve adjacent the air outlet end for normally pulling the adjacent portions of said walls together at the air outlet end to close said air outlet.

24. The device of claim 23, includes:

at least a first rib protruding inward from the inside of said tube opposed to one of said walls of the sleeve; and at least a second rib protruding inward from the inside of said tube opposed to the other of said wall of the sleeve, said ribs spacing said sleeve from the inside surface of the tube.

* * * * *